US012806380B2

(12) United States Patent
Vo

(10) Patent No.: US 12,806,380 B2
(45) Date of Patent: Nov. 24, 2026

(54) APPLICATOR FOR DISEASE MANAGEMENT SYSTEM

(71) Applicant: Willow Laboratories, Inc., Irvine, CA (US)

(72) Inventor: Hung The Vo, Fountain Valley, CA (US)

(73) Assignee: Willow Laboratories, Inc., Irvine, CA (US)

( * ) Notice: Subject to any disclaimer, the term of this patent is extended or adjusted under 35 U.S.C. 154(b) by 1042 days.

(21) Appl. No.: 17/817,607

(22) Filed: Aug. 4, 2022

(65) Prior Publication Data

US 2023/0045647 A1 Feb. 9, 2023

Related U.S. Application Data

(60) Provisional application No. 63/229,297, filed on Aug. 4, 2021.

(51) Int. Cl.

*A61M 25/06* (2006.01)
*A61B 5/024* (2006.01)
*A61B 5/145* (2006.01)

(52) U.S. Cl.

CPC ............. *A61M 25/06* (2013.01); *A61B 5/024* (2013.01); *A61B 5/14503* (2013.01); *A61B 5/14532* (2013.01); *A61B 2560/063* (2013.01)

(58) Field of Classification Search

None

See application file for complete search history.

(56) References Cited

U.S. PATENT DOCUMENTS

| | | | |
|---|---|---|---|
| 4,919,596 | A | 4/1990 | Slate et al. |
| 4,960,128 | A | 10/1990 | Gordon et al. |
| 4,964,408 | A | 10/1990 | Hink et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |

(Continued)

FOREIGN PATENT DOCUMENTS

WO WO-2017219155 A1 * 12/2017 ............. A61M 5/46

OTHER PUBLICATIONS

US 2022/0192529 A1, 06/2022, Al-Ali et al. (withdrawn)

(Continued)

*Primary Examiner* — Manuel A Mendez

(74) *Attorney, Agent, or Firm* — KNOBBE, MARTENS, OLSON & BEAR, LLP

(57) ABSTRACT

One or more insertion mechanisms may be configured to insert and retract one or more needles associated with a component configured to implantable component into the tissue of a patient. For example, a component or implantable component may include a cannula for delivery of medication to a patient or an analyte sensor. An insertion mechanism may be configured to be part of or enclosed within a structure of the Disease Management System. For example, an insertion mechanism may be configured to operate within the structure of the Disease Management System and not require outside components or devices to apply one or more needles or implantable components to the patient.

21 Claims, 7 Drawing Sheets

(56) References Cited

U.S. PATENT DOCUMENTS

| | | | |
|---|---|---|---|
| D359,546 S | 6/1995 | Savage et al. | |
| 5,431,170 A | 7/1995 | Mathews | |
| 5,436,499 A | 7/1995 | Namavar et al. | |
| D361,840 S | 8/1995 | Savage et al. | |
| D362,063 S | 9/1995 | Savage et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,590,649 A | 1/1997 | Caro et al. | |
| 5,602,924 A | 2/1997 | Durand et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,671,914 A | 9/1997 | Kalkhoran et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,890,929 A | 4/1999 | Mills et al. | |
| 5,919,134 A | 7/1999 | Diab | |
| 5,957,895 A * | 9/1999 | Sage | A61M 5/14586 604/185 |
| 5,987,343 A | 11/1999 | Kinast | |
| 5,997,343 A | 12/1999 | Mills et al. | |
| 6,002,952 A | 12/1999 | Diab et al. | |
| 6,010,937 A | 1/2000 | Karam et al. | |
| 6,027,452 A | 2/2000 | Flaherty et al. | |
| 6,040,578 A | 3/2000 | Malin et al. | |
| 6,066,204 A | 5/2000 | Haven | |
| 6,083,248 A | 7/2000 | Thompson | |
| 6,115,673 A | 9/2000 | Malin et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,152,754 A | 11/2000 | Gerhardt et al. | |
| 6,184,521 B1 | 2/2001 | Coffin, IV et al. | |
| 6,232,609 B1 | 5/2001 | Snyder et al. | |
| 6,241,683 B1 | 6/2001 | Macklem et al. | |
| 6,253,097 B1 | 6/2001 | Aronow et al. | |
| 6,255,708 B1 | 7/2001 | Sudharsanan et al. | |
| 6,280,381 B1 | 8/2001 | Malin et al. | |
| 6,285,896 B1 | 9/2001 | Tobler et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,334,065 B1 | 12/2001 | Al-Ali et al. | |
| 6,360,114 B1 | 3/2002 | Diab et al. | |
| 6,368,283 B1 | 4/2002 | Xu et al. | |
| 6,411,373 B1 | 6/2002 | Garside et al. | |
| 6,415,167 B1 | 7/2002 | Blank et al. | |
| 6,423,035 B1 | 7/2002 | Das et al. | |
| 6,427,088 B1 | 7/2002 | Bowman et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,487,429 B2 | 11/2002 | Hockersmith et al. | |
| 6,505,059 B1 | 1/2003 | Kollias et al. | |
| 6,525,386 B1 | 2/2003 | Mills et al. | |
| 6,526,300 B1 | 2/2003 | Kiani et al. | |
| 6,534,012 B1 | 3/2003 | Hazen et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,587,196 B1 | 7/2003 | Stippick et al. | |
| 6,587,199 B1 | 7/2003 | Luu | |
| 6,595,316 B2 | 7/2003 | Cybulski et al. | |
| 6,597,932 B2 | 7/2003 | Tian et al. | |
| 6,606,511 B1 | 8/2003 | Ali et al. | |
| 6,635,559 B2 | 10/2003 | Greenwald et al. | |
| 6,639,668 B1 | 10/2003 | Trepagnier | |
| 6,640,116 B2 | 10/2003 | Diab | |
| 6,640,117 B2 | 10/2003 | Makarewicz et al. | |
| 6,658,276 B2 | 12/2003 | Kiani et al. | |
| 6,661,161 B1 | 12/2003 | Lanzo et al. | |
| 6,697,656 B1 | 2/2004 | Ai-Ali | |
| 6,697,658 B2 | 2/2004 | Al-Ali | |
| RE38,476 E | 3/2004 | Diab et al. | |
| RE38,492 E | 4/2004 | Diab et al. | |
| 6,738,652 B2 | 5/2004 | Mattu et al. | |
| 6,760,607 B2 | 7/2004 | Al-Ali | |
| 6,788,965 B2 | 9/2004 | Ruchti et al. | |
| 6,816,241 B2 | 11/2004 | Grubisic | |
| 6,822,564 B2 | 11/2004 | Al-Ali | |
| 6,850,787 B2 | 2/2005 | Weber et al. | |
| 6,850,788 B2 | 2/2005 | Al-Ali | |
| 6,876,931 B2 | 4/2005 | Lorenz et al. | |
| 6,916,159 B2 | 7/2005 | Rush et al. | |
| 6,920,345 B2 | 7/2005 | Al-Ali et al. | |
| 6,934,570 B2 | 8/2005 | Kiani et al. | |
| 6,943,348 B1 | 9/2005 | Coffin IV | |
| 6,956,649 B2 | 10/2005 | Acosta et al. | |
| 6,961,598 B2 | 11/2005 | Diab | |
| 6,970,792 B1 | 11/2005 | Diab | |
| 6,985,764 B2 | 1/2006 | Mason et al. | |
| 6,990,364 B2 | 1/2006 | Ruchti et al. | |
| 6,998,247 B2 | 2/2006 | Monfre et al. | |
| 7,003,338 B2 | 2/2006 | Weber et al. | |
| 7,015,451 B2 | 3/2006 | Dalke et al. | |
| 7,027,849 B2 | 4/2006 | Al-Ali | |
| D526,719 S | 8/2006 | Richie, Jr. et al. | |
| 7,096,052 B2 | 8/2006 | Mason et al. | |
| 7,096,054 B2 | 8/2006 | Abdul-Hafiz et al. | |
| D529,616 S | 10/2006 | Deros et al. | |
| 7,133,710 B2 | 11/2006 | Acosta et al. | |
| 7,142,901 B2 | 11/2006 | Kiani et al. | |
| 7,225,006 B2 | 5/2007 | Al-Ali et al. | |
| RE39,672 E | 6/2007 | Shehada et al. | |
| 7,254,429 B2 | 8/2007 | Schurman et al. | |
| 7,254,431 B2 | 8/2007 | Al-Ali et al. | |
| 7,254,434 B2 | 8/2007 | Schulz et al. | |
| 7,274,955 B2 | 9/2007 | Kiani et al. | |
| D554,263 S | 10/2007 | Al-Ali et al. | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| 7,341,559 B2 | 3/2008 | Schulz et al. | |
| 7,343,186 B2 | 3/2008 | Lamego et al. | |
| D566,282 S | 4/2008 | Al-Ali et al. | |
| 7,356,365 B2 | 4/2008 | Schurman | |
| 7,371,981 B2 | 5/2008 | Abdul-Hafiz | |
| 7,373,193 B2 | 5/2008 | Al-Ali et al. | |
| 7,377,794 B2 | 5/2008 | Al-Ali et al. | |
| 7,395,158 B2 | 7/2008 | Monfre et al. | |
| 7,415,297 B2 | 8/2008 | Al-Ali et al. | |
| 7,438,683 B2 | 10/2008 | Al-Ali et al. | |
| 7,483,729 B2 | 1/2009 | Al-Ali et al. | |
| D587,657 S | 3/2009 | Al-Ali et al. | |
| 7,500,950 B2 | 3/2009 | Al-Ali et al. | |
| 7,509,494 B2 | 3/2009 | Al-Ali | |
| 7,510,849 B2 | 3/2009 | Schurman et al. | |
| 7,514,725 B2 | 4/2009 | Wojtczuk et al. | |
| 7,519,406 B2 | 4/2009 | Blank et al. | |
| D592,507 S | 5/2009 | Wachman et al. | |
| 7,530,942 B1 | 5/2009 | Diab | |
| 7,547,281 B2 | 6/2009 | Hayes et al. | |
| 7,593,230 B2 | 9/2009 | Abul-Haj et al. | |
| 7,596,398 B2 | 9/2009 | Al-Ali et al. | |
| 7,606,608 B2 | 10/2009 | Blank et al. | |
| 7,620,674 B2 | 11/2009 | Ruchti et al. | |
| D606,659 S | 12/2009 | Kiani et al. | |
| 7,629,039 B2 | 12/2009 | Eckerbom et al. | |
| 7,640,140 B2 | 12/2009 | Ruchti et al. | |
| 7,647,083 B2 | 1/2010 | Al-Ali et al. | |
| D609,193 S | 2/2010 | Al-Ali et al. | |
| D614,305 S | 4/2010 | Al-Ali et al. | |

(56) References Cited

U.S. PATENT DOCUMENTS 7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,761,127 B2 7/2010 Al-Ali et al.
7,764,982 B2 7/2010 Dalke et al.
D621,516 S 8/2010 Kiani et al.
7,791,155 B2 9/2010 Diab
RE41,912 E 11/2010 Parker
7,880,626 B2 2/2011 Al-Ali et al.
7,909,772 B2 3/2011 Popov et al.
7,919,713 B2 4/2011 Al-Ali et al.
7,937,128 B2 5/2011 Al-Ali
7,937,129 B2 5/2011 Mason et al.
7,941,199 B2 5/2011 Kiani
7,957,780 B2 6/2011 Lamego et al.
7,962,188 B2 6/2011 Kiani et al.
7,976,472 B2 7/2011 Kiani
7,990,382 B2 8/2011 Kiani
7,999,674 B2 8/2011 Kamen
8,008,088 B2 8/2011 Bellott et al.
RE42,753 E 9/2011 Kiani-Azarbayjany et al.
8,028,701 B2 10/2011 Al-Ali et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,118,782 B2 2/2012 Remde
8,130,105 B2 3/2012 Al-Ali et al.
8,182,443 B1 5/2012 Kiani
8,190,223 B2 5/2012 Al-Ali et al.
8,192,394 B2 6/2012 Estes et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,255,026 B1 8/2012 Ai-Ali
8,265,723 B1 9/2012 McHale et al.
8,274,360 B2 9/2012 Sampath et al.
8,280,473 B2 10/2012 Al-Ali
8,294,581 B2 10/2012 Kamen
8,315,683 B2 11/2012 Al-Ali et al.
RE43,860 E 12/2012 Parker
8,333,714 B2 12/2012 Stafford
8,346,330 B2 1/2013 Lamego
8,353,842 B2 1/2013 Al-Ali et al.
8,355,766 B2 1/2013 MacNeish et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,414,563 B2 4/2013 Kamen et al.
8,418,524 B2 4/2013 Al-Ali
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,707 B2 6/2013 Kiani
8,471,713 B2 6/2013 Poeze et al.
8,473,020 B2 6/2013 Kiani et al.
8,509,867 B2 8/2013 Workman et al.
8,515,509 B2 8/2013 Bruinsma et al.
8,523,781 B2 9/2013 Al-Ali
8,527,298 B2 9/2013 Darling et al.
D692,145 S 10/2013 Al-Ali et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,584,345 B2 11/2013 Al-Ali et al.
8,585,377 B2 11/2013 Kamen
8,588,880 B2 11/2013 Abdul-Hafiz et al.
8,597,274 B2 12/2013 Sloan et al.
8,613,724 B2 12/2013 Lanier et al.
8,630,691 B2 1/2014 Lamego et al.
8,641,631 B2 2/2014 Sierra et al.
8,652,060 B2 2/2014 Al-Ali
8,666,468 B1 3/2014 Ai-Ali
8,670,811 B2 3/2014 O'Reilly
8,679,060 B2 3/2014 Mernoe et al.
RE44,823 E 4/2014 Parker
RE44,875 E 4/2014 Kiani et al.
8,688,183 B2 4/2014 Bruinsma et al.
8,690,799 B2 4/2014 Telfort et al.
8,702,627 B2 4/2014 Telfort et al.
8,712,494 B1 4/2014 MacNeish, III et al.
8,715,206 B2 5/2014 Telfort et al.
8,723,677 B1 5/2014 Kiani
8,740,792 B1 6/2014 Kiani et al.
8,755,535 B2 6/2014 Telfort et al.
8,755,872 B1 6/2014 Marinow
8,764,671 B2 7/2014 Kiani
8,768,423 B2 7/2014 Shakespeare et al.
8,771,204 B2 7/2014 Telfort et al.
8,781,544 B2 7/2014 Al-Ali et al.
8,784,364 B2 7/2014 Kamen et al.
8,790,268 B2 7/2014 Al-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,840,549 B2 9/2014 Al-Ali et al.
8,852,094 B2 10/2014 Al-Ali et al.
8,852,994 B2 10/2014 Wojtczuk et al.
8,862,198 B2 10/2014 Stafford
8,897,847 B2 11/2014 Al-Ali
8,911,377 B2 12/2014 Ai-Ali
8,980,186 B2 3/2015 Chen et al.
8,989,831 B2 3/2015 Al-Ali et al.
8,998,809 B2 4/2015 Kiani
9,066,666 B2 6/2015 Kiani
9,066,680 B1 6/2015 Al-Ali et al.
9,095,316 B2 8/2015 Welch et al.
9,106,038 B2 8/2015 Telfort et al.
9,107,625 B2 8/2015 Telfort et al.
9,131,881 B2 9/2015 Diab et al.
9,132,227 B2 9/2015 Bryant et al.
9,138,180 B1 9/2015 Coverston et al.
9,153,112 B1 10/2015 Kiani et al.
9,180,245 B2 11/2015 Bryant et al.
9,186,098 B2 11/2015 Lee et al.
9,192,329 B2 11/2015 Al-Ali
9,192,351 B1 11/2015 Telfort et al.
9,195,385 B2 11/2015 Al-Ali et al.
9,205,188 B2 12/2015 Lanigan et al.
9,211,095 B1 12/2015 Al-Ali
9,215,992 B2 12/2015 Donnay et al.
9,218,454 B2 12/2015 Kiani et al.
9,245,668 B1 1/2016 Vo et al.
9,265,453 B2 2/2016 Curry et al.
9,267,572 B2 2/2016 Barker et al.
9,277,880 B2 3/2016 Poeze et al.
9,307,928 B1 4/2016 Al-Ali et al.
9,323,894 B2 4/2016 Kiani
D755,392 S 5/2016 Hwang et al.
9,326,712 B1 5/2016 Kiani
9,392,945 B2 7/2016 Al-Ali et al.
9,402,544 B2 8/2016 Yee et al.
9,408,542 B1 8/2016 Kinast et al.
9,436,645 B2 9/2016 Al-Ali et al.
9,445,759 B1 9/2016 Lamego et al.
9,474,474 B2 10/2016 Lamego et al.
9,480,435 B2 11/2016 Olsen
9,510,779 B2 12/2016 Poeze et al.
9,517,024 B2 12/2016 Kiani et al.
9,532,722 B2 1/2017 Lamego et al.
9,560,996 B2 2/2017 Kiani
9,579,039 B2 2/2017 Jansen et al.
9,604,001 B2 3/2017 Kamen
9,622,692 B2 4/2017 Lamego et al.
D788,312 S 5/2017 Al-Ali et al.

(56) References Cited

U.S. PATENT DOCUMENTS 9,636,068 B2 5/2017 Yee et al.
9,649,054 B2 5/2017 Lamego et al.
9,669,161 B2 6/2017 Bryant et al.
9,687,183 B2 6/2017 Donnay et al.
9,687,602 B2 6/2017 Murphy et al.
9,697,928 B2 7/2017 Al-Ali et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,737,656 B2 8/2017 Rosinko
9,749,232 B2 8/2017 Sampath et al.
9,750,442 B2 9/2017 Olsen
9,750,461 B1 9/2017 Telfort
9,750,896 B2 9/2017 Kamen et al.
9,775,545 B2 10/2017 Al-Ali et al.
9,778,079 B1 10/2017 Al-Ali et al.
9,782,077 B2 10/2017 Lamego et al.
9,787,568 B2 10/2017 Lamego et al.
9,808,188 B1 11/2017 Perea et al.
9,839,379 B2 12/2017 Al-Ali et al.
9,839,381 B1 12/2017 Weber et al.
9,847,749 B2 12/2017 Kiani et al.
9,848,800 B1 12/2017 Lee et al.
9,861,298 B2 1/2018 Eckerbom et al.
9,861,305 B1 1/2018 Weber et al.
9,861,792 B2 * 1/2018 Hall ...................... A61M 29/00
9,877,650 B2 1/2018 Muhsin et al.
9,891,079 B2 2/2018 Dalvi
9,924,897 B1 3/2018 Abdul-Hafiz
9,931,461 B2 4/2018 Kamen et al.
9,936,917 B2 4/2018 Poeze et al.
9,955,937 B2 5/2018 Telfort
9,965,946 B2 5/2018 Al-Ali et al.
9,968,730 B2 5/2018 Blumberg et al.
9,980,670 B2 5/2018 Funderburk et al.
D820,865 S 6/2018 Muhsin et al.
9,986,952 B2 6/2018 Dalvi et al.
9,993,188 B2 6/2018 Yee et al.
D822,215 S 7/2018 Al-Ali et al.
D822,216 S 7/2018 Barker et al.
10,010,276 B2 7/2018 Al-Ali et al.
10,010,280 B2 7/2018 Donnay et al.
10,086,138 B1 10/2018 Novak, Jr.
10,105,286 B2 10/2018 Lanier et al.
10,111,591 B2 10/2018 Dyell et al.
D833,624 S 11/2018 DeJong et al.
10,123,729 B2 11/2018 Dyell et al.
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,348 B2 1/2019 Al-Ali et al.
RE47,218 E 2/2019 Al-Ali
RE47,244 E 2/2019 Kiani et al.
RE47,249 E 2/2019 Kiani et al.
10,195,343 B2 2/2019 Kamen et al.
10,205,291 B2 2/2019 Scruggs et al.
10,226,187 B2 3/2019 Al-Ali et al.
10,231,657 B2 3/2019 Al-Ali et al.
10,231,670 B2 3/2019 Blank et al.
10,232,113 B2 3/2019 Palerm
10,238,794 B2 3/2019 Kamen et al.
10,242,159 B2 3/2019 Kamen et al.
RE47,353 E 4/2019 Kiani et al.
10,279,247 B2 5/2019 Kiani
10,292,664 B2 5/2019 Al-Ali
10,299,720 B2 5/2019 Brown et al.
10,327,337 B2 6/2019 Schmidt et al.
10,327,713 B2 6/2019 Barker et al.
10,332,630 B2 6/2019 Al-Ali
10,362,972 B2 7/2019 Stafford
10,363,342 B2 7/2019 Dillon et al.
10,383,520 B2 8/2019 Wojtczuk et al.
10,383,527 B2 8/2019 Al-Ali
10,388,120 B2 8/2019 Muhsin et al.
D864,120 S 10/2019 Forrest et al.
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.
10,456,064 B2 10/2019 Peterson et al.
10,456,090 B2 10/2019 Thorpe et al.
10,463,340 B2 11/2019 Telfort et al.
10,471,159 B1 11/2019 Lapotko et al.
10,505,311 B2 12/2019 Al-Ali et al.
10,524,738 B2 1/2020 Olsen
10,532,174 B2 1/2020 Al-Ali
10,537,285 B2 1/2020 Shreim et al.
10,542,903 B2 1/2020 Al-Ali et al.
10,555,678 B2 2/2020 Dalvi et al.
10,568,553 B2 2/2020 O'Neil et al.
10,608,817 B2 3/2020 Haider et al.
D880,477 S 4/2020 Forrest et al.
D882,432 S 4/2020 Yee et al.
10,617,302 B2 4/2020 Al-Ali et al.
10,617,335 B2 4/2020 Al-Ali et al.
10,637,181 B2 4/2020 Al-Ali et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
D890,708 S 7/2020 Forrest et al.
10,721,785 B2 7/2020 Al-Ali
10,736,518 B2 8/2020 Al-Ali et al.
10,750,984 B2 8/2020 Pauley et al.
D897,098 S 9/2020 Al-Ali
10,779,098 B2 9/2020 Iswanto et al.
10,786,190 B2 9/2020 Yee et al.
10,827,961 B1 11/2020 Iyengar et al.
10,828,007 B1 11/2020 Telfort et al.
10,832,818 B2 11/2020 Muhsin et al.
10,849,554 B2 12/2020 Shreim et al.
10,856,750 B2 12/2020 Indorf
D906,970 S 1/2021 Forrest et al.
D908,213 S 1/2021 Abdul-Hafiz et al.
10,881,341 B1 1/2021 Curry et al.
10,905,377 B2 2/2021 Gray et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,952,657 B2 3/2021 Curry et al.
10,956,950 B2 3/2021 Al-Ali et al.
10,959,654 B2 3/2021 Curry et al.
D916,135 S 4/2021 Indorf et al.
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,000,216 B2 5/2021 Curry et al.
11,000,645 B2 5/2021 Estes et al.
11,006,867 B2 5/2021 Ai-Ali
11,006,870 B2 5/2021 Yee et al.
11,006,871 B2 5/2021 Yee et al.
11,006,872 B2 5/2021 Yee et al.
D921,202 S 6/2021 Al-Ali et al.
11,024,064 B2 6/2021 Muhsin et al.
11,026,604 B2 6/2021 Chen et al.
D925,597 S 7/2021 Chandran et al.
D927,699 S 8/2021 Al-Ali et al.
11,076,777 B2 8/2021 Lee et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.

(56) References Cited

U.S. PATENT DOCUMENTS 11,134,896 B2 * 10/2021 Gray .................... A61B 5/0004
11,145,408 B2 10/2021 Sampath et al.
11,147,518 B1 10/2021 Al-Ali et al.
11,166,656 B2 11/2021 Yee et al.
11,185,262 B2 11/2021 Al-Ali et al.
11,191,484 B2 12/2021 Kiani et al.
11,202,591 B2 12/2021 Yee et al.
11,213,229 B2 1/2022 Yee et al.
11,241,534 B2 2/2022 Miller et al.
D946,596 S 3/2022 Ahmed
D946,597 S 3/2022 Ahmed
D946,598 S 3/2022 Ahmed
D946,617 S 3/2022 Ahmed
11,266,335 B2 3/2022 Donnay et al.
11,272,839 B2 3/2022 Al-Ali et al.
11,289,199 B2 3/2022 Al-Ali
RE49,034 E 4/2022 Al-Ali
11,298,021 B2 4/2022 Muhsin et al.
D950,580 S 5/2022 Ahmed
D950,599 S 5/2022 Ahmed
D950,738 S 5/2022 Al-Ali et al.
D957,648 S 7/2022 Ai-Ali
11,376,362 B2 7/2022 Mazlish
11,382,567 B2 7/2022 O'Brien et al.
11,386,482 B2 7/2022 Estes
11,389,093 B2 7/2022 Triman et al.
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
11,446,439 B2 9/2022 Mazlish et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
11,511,039 B2 11/2022 Mazlish et al.
D971,933 S 12/2022 Ahmed
D973,072 S 12/2022 Ahmed
D973,685 S 12/2022 Ahmed
D973,686 S 12/2022 Ahmed
D974,193 S 1/2023 Forrest et al.
D974,564 S 1/2023 Stafford
D979,516 S 2/2023 Al-Ali et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,684,716 B2 6/2023 Zheng et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
11,737,783 B2 8/2023 Garai
D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,766,198 B2 9/2023 Pauley et al.
D1,000,975 S 10/2023 Al-Ali et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,014,328 B2 6/2024 Wachman et al.
D1,036,293 S 7/2024 Al-Ali et al.
D1,037,462 S 7/2024 Al-Ali et al.
12,029,844 B2 7/2024 Pauley et al.
12,042,145 B2 7/2024 List
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
12,097,352 B2 9/2024 O'Connor et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 10/2024 Kiani et al.
12,131,661 B2 10/2024 Pauley et al.
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Al-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin
D1,066,244 S 3/2025 Lim et al.
D1,066,672 S 3/2025 Al-Ali et al.
12,246,160 B2 3/2025 Cardinali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
12,296,139 B2 5/2025 Estes
12,300,375 B2 5/2025 Nazzaro et al.
12,303,667 B2 5/2025 Desborough et al.
12,303,668 B2 5/2025 Mazlish et al.
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.
12,343,501 B2 7/2025 Zheng et al.
12,343,502 B2 7/2025 Mazlish et al.
12,362,596 B2 7/2025 Barker et al.
12,370,307 B2 7/2025 Lee et al.
12,370,309 B2 7/2025 Lee et al.
12,383,166 B2 8/2025 Desborough et al.
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,403,245 B2 9/2025 Estes et al.
12,403,257 B2 9/2025 Estes et al.
12,406,760 B2 9/2025 Zade et al.

(56) References Cited

U.S. PATENT DOCUMENTS

| | | | |
|---|---|---|---|
| 12,409,270 B2 | 9/2025 | Lee et al. | |
| 12,427,251 B2 | 9/2025 | Lee et al. | |
| 12,429,141 B2 | 9/2025 | McLaughlin et al. | |
| 12,431,229 B2 | 9/2025 | Lee et al. | |
| 12,433,512 B2 | 10/2025 | Nazzaro et al. | |
| 12,433,524 B2 | 10/2025 | Al-Ali et al. | |
| 12,433,998 B2 | 10/2025 | O'Connor et al. | |
| 12,440,128 B2 | 10/2025 | Al-Ali et al. | |
| 12,440,617 B2 | 10/2025 | Nazzaro | |
| D1,102,622 S | 11/2025 | Al-Ali et al. | |
| 12,478,272 B2 | 11/2025 | Telfort et al. | |
| 12,478,293 B1 | 11/2025 | Al-Ali et al. | |
| D1,106,466 S | 12/2025 | Avendaño et al. | |
| 12,495,967 B2 | 12/2025 | Muhsin et al. | |
| 12,495,999 B2 | 12/2025 | Al-Ali et al. | |
| 12,507,952 B2 | 12/2025 | Al-Ali et al. | |
| 12,521,021 B2 | 1/2026 | Al-Ali et al. | |
| 12,521,506 B2 | 1/2026 | Yu et al. | |
| 12,538,084 B1 | 1/2026 | Telfort et al. | |
| 12,539,046 B2 | 2/2026 | Kiani | |
| D1,119,639 S | 3/2026 | Al-Ali et al. | |
| 12,575,797 B2 | 3/2026 | Olsen et al. | |
| D1,124,008 S | 4/2026 | Indorf et al. | |
| D1,124,017 S | 4/2026 | Indorf et al. | |
| D1,124,917 S | 5/2026 | Al-Ali et al. | |
| D1,127,209 S | 5/2026 | Al-Ali et al. | |
| 12,616,623 B1 | 5/2026 | Al-Ali et al. | |
| 2001/0034477 A1 | 10/2001 | Mansfield et al. | |
| 2001/0037083 A1 | 11/2001 | Hartlaub et al. | |
| 2001/0039483 A1 | 11/2001 | Brand et al. | |
| 2002/0010401 A1 | 1/2002 | Bushmakin et al. | |
| 2002/0058864 A1 | 5/2002 | Mansfield et al. | |
| 2002/0133080 A1 | 9/2002 | Apruzzese et al. | |
| 2003/0013975 A1 | 1/2003 | Kiani | |
| 2003/0018243 A1 | 1/2003 | Gerhardt et al. | |
| 2003/0144582 A1 | 7/2003 | Cohen et al. | |
| 2003/0156288 A1 | 8/2003 | Barnum et al. | |
| 2003/0212312 A1 | 11/2003 | Coffin, IV et al. | |
| 2004/0106163 A1 | 6/2004 | Workman, Jr. et al. | |
| 2004/0162521 A1* | 8/2004 | Bengtsson | A61B 5/1518 604/173 |
| 2005/0055276 A1 | 3/2005 | Kiani et al. | |
| 2005/0234317 A1 | 10/2005 | Kiani | |
| 2006/0073719 A1 | 4/2006 | Kiani | |
| 2006/0189871 A1 | 8/2006 | Al-Ali et al. | |
| 2007/0073116 A1 | 3/2007 | Kiani et al. | |
| 2007/0093754 A1* | 4/2007 | Mogensen | A61M 5/158 604/164.12 |
| 2007/0180140 A1 | 8/2007 | Welch et al. | |
| 2007/0244377 A1 | 10/2007 | Cozad et al. | |
| 2008/0064965 A1 | 3/2008 | Jay et al. | |
| 2008/0094228 A1 | 4/2008 | Welch et al. | |
| 2008/0103375 A1 | 5/2008 | Kian | |
| 2008/0194934 A1 | 8/2008 | Ray et al. | |
| 2008/0221418 A1 | 9/2008 | Al-Ali et al. | |
| 2008/0243085 A1* | 10/2008 | DeStefano | A61M 5/158 604/180 |
| 2009/0036759 A1 | 2/2009 | Ault et al. | |
| 2009/0093687 A1 | 4/2009 | Telfort et al. | |
| 2009/0095926 A1 | 4/2009 | MacNeish, III | |
| 2009/0247984 A1 | 10/2009 | Lamego et al. | |
| 2009/0275844 A1 | 11/2009 | Al-Ali | |
| 2010/0004518 A1 | 1/2010 | Vo et al. | |
| 2010/0030040 A1 | 2/2010 | Poeze et al. | |
| 2010/0099964 A1 | 4/2010 | O'Reilly et al. | |
| 2010/0152665 A1* | 6/2010 | Hasted | A61M 5/158 604/164.12 |
| 2010/0234718 A1 | 9/2010 | Sampath et al. | |
| 2010/0270257 A1 | 10/2010 | Wachman et al. | |
| 2011/0028806 A1 | 2/2011 | Merritt et al. | |
| 2011/0028809 A1 | 2/2011 | Goodman | |
| 2011/0040197 A1 | 2/2011 | Welch et al. | |
| 2011/0082711 A1 | 4/2011 | Poeze et al. | |
| 2011/0087081 A1 | 4/2011 | Kiani et al. | |
| 2011/0098548 A1 | 4/2011 | Budiman et al. | |
| 2011/0118561 A1 | 5/2011 | Tari et al. | |
| 2011/0137297 A1 | 6/2011 | Kiani et al. | |
| 2011/0172498 A1 | 7/2011 | Olsen et al. | |
| 2011/0208155 A1 | 8/2011 | Palerm et al. | |
| 2012/0123231 A1 | 5/2012 | O'Reilly | |
| 2012/0165629 A1 | 6/2012 | Merritt et al. | |
| 2012/0209084 A1 | 8/2012 | Olsen et al. | |
| 2012/0226117 A1 | 9/2012 | Lamego et al. | |
| 2012/0283524 A1 | 11/2012 | Kiani et al. | |
| 2013/0023775 A1 | 1/2013 | Lamego et al. | |
| 2013/0060147 A1 | 3/2013 | Welch et al. | |
| 2013/0096405 A1 | 4/2013 | Garfio | |
| 2013/0296672 A1 | 11/2013 | O'Neil et al. | |
| 2013/0345663 A1 | 12/2013 | Agrawal et al. | |
| 2013/0345921 A1 | 12/2013 | Al-Ali et al. | |
| 2014/0107607 A1 | 4/2014 | Estes | |
| 2014/0166076 A1 | 6/2014 | Kiani et al. | |
| 2014/0180160 A1 | 6/2014 | Brown et al. | |
| 2014/0187973 A1 | 7/2014 | Brown et al. | |
| 2014/0275871 A1 | 9/2014 | Lamego et al. | |
| 2014/0275872 A1 | 9/2014 | Merritt et al. | |
| 2014/0316217 A1 | 10/2014 | Purdon et al. | |
| 2014/0316218 A1 | 10/2014 | Purdon et al. | |
| 2014/0323897 A1 | 10/2014 | Brown et al. | |
| 2014/0323898 A1 | 10/2014 | Purdon et al. | |
| 2015/0005600 A1 | 1/2015 | Blank et al. | |
| 2015/0011907 A1 | 1/2015 | Purdon et al. | |
| 2015/0073241 A1 | 3/2015 | Lamego | |
| 2015/0080754 A1 | 3/2015 | Purdon et al. | |
| 2015/0099950 A1 | 4/2015 | Al-Ali et al. | |
| 2016/0196388 A1 | 7/2016 | Lamego | |
| 2016/0367173 A1 | 12/2016 | Dalvi et al. | |
| 2017/0024748 A1 | 1/2017 | Haider | |
| 2017/0173632 A1 | 6/2017 | Al-Ali | |
| 2017/0251974 A1 | 9/2017 | Shreim et al. | |
| 2018/0242926 A1 | 8/2018 | Muhsin et al. | |
| 2018/0247712 A1 | 8/2018 | Muhsin et al. | |
| 2019/0239787 A1 | 8/2019 | Pauley et al. | |
| 2019/0320906 A1 | 10/2019 | Olsen | |
| 2019/0374713 A1 | 12/2019 | Kiani et al. | |
| 2020/0060869 A1 | 2/2020 | Telfort et al. | |
| 2020/0111552 A1 | 4/2020 | Ahmed | |
| 2020/0113520 A1 | 4/2020 | Abdul-Hafiz et al. | |
| 2020/0138368 A1 | 5/2020 | Kiani et al. | |
| 2020/0163597 A1 | 5/2020 | Dalvi et al. | |
| 2020/0196877 A1 | 6/2020 | Vo et al. | |
| 2020/0253474 A1 | 8/2020 | Muhsin et al. | |
| 2020/0253544 A1 | 8/2020 | Belur Nagaraj et al. | |
| 2020/0275841 A1 | 9/2020 | Telfort et al. | |
| 2020/0288983 A1 | 9/2020 | Telfort et al. | |
| 2020/0321793 A1 | 10/2020 | Al-Ali et al. | |
| 2020/0329983 A1 | 10/2020 | Al-Ali et al. | |
| 2020/0329984 A1 | 10/2020 | Al-Ali et al. | |
| 2020/0329993 A1 | 10/2020 | Al-Ali et al. | |
| 2020/0330037 A1 | 10/2020 | Al-Ali et al. | |
| 2021/0022628 A1 | 1/2021 | Telfort et al. | |
| 2021/0104173 A1 | 4/2021 | Pauley et al. | |
| 2021/0113121 A1 | 4/2021 | Diab et al. | |
| 2021/0117525 A1 | 4/2021 | Kiani et al. | |
| 2021/0118581 A1 | 4/2021 | Kiani et al. | |
| 2021/0121582 A1 | 4/2021 | Krishnamani et al. | |
| 2021/0161465 A1 | 6/2021 | Barker et al. | |
| 2021/0236729 A1 | 8/2021 | Kiani et al. | |
| 2021/0236730 A1 | 8/2021 | Lee et al. | |
| 2021/0256267 A1 | 8/2021 | Ranasinghe et al. | |
| 2021/0256835 A1 | 8/2021 | Ranasinghe et al. | |
| 2021/0275101 A1 | 9/2021 | Vo et al. | |
| 2021/0290060 A1 | 9/2021 | Ahmed | |
| 2021/0290072 A1 | 9/2021 | Forrest | |
| 2021/0290080 A1 | 9/2021 | Ahmed | |
| 2021/0290120 A1 | 9/2021 | Al-Ali | |
| 2021/0290177 A1 | 9/2021 | Novak, Jr. | |
| 2021/0290184 A1 | 9/2021 | Ahmed | |
| 2021/0296008 A1 | 9/2021 | Novak, Jr. | |
| 2021/0330228 A1 | 10/2021 | Olsen et al. | |
| 2021/0379282 A1 | 12/2021 | O'Connor et al. | |
| 2021/0386382 A1 | 12/2021 | Olsen et al. | |
| 2021/0402110 A1 | 12/2021 | Pauley et al. | |
| 2022/0026355 A1 | 1/2022 | Normand et al. | |

(56) References Cited

U.S. PATENT DOCUMENTS

| | | | |
|---|---|---|---|
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0168500 A1 | 6/2022 | McCaffrey |
| 2022/0218244 A1 | 7/2022 | Kiani et al. |
| 2022/0218897 A1 | 7/2022 | Nazzaro |
| 2022/0287574 A1 | 9/2022 | Telfort et al. |
| 2022/0288311 A1 | 9/2022 | Lee et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0234066 A9 | 7/2024 | Wiel et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |
| 2025/0037836 A1 | 1/2025 | Kiani |
| 2025/0100482 A1 | 3/2025 | Al-Ali et al. |
| 2025/0118415 A1 | 4/2025 | Olsen |
| 2025/0135114 A1 | 5/2025 | Bussiere et al. |
| 2025/0144295 A1 | 5/2025 | Zheng et al. |
| 2025/0205427 A1 | 6/2025 | Lee et al. |
| 2025/0246285 A1 | 7/2025 | Alles et al. |
| 2025/0255764 A1 | 8/2025 | Stead |
| 2025/0278512 A1 | 9/2025 | Koo et al. |
| 2025/0281059 A1 | 9/2025 | Avendano |
| 2025/0281078 A1 | 9/2025 | Desborough et al. |
| 2025/0281688 A1 | 9/2025 | Estes |
| 2025/0288250 A1 | 9/2025 | Al-Ali et al. |
| 2025/0295366 A1 | 9/2025 | Al-Ali et al. |
| 2025/0302426 A1 | 10/2025 | Ha et al. |
| 2025/0311949 A1 | 10/2025 | Al-Ali et al. |
| 2025/0318761 A1 | 10/2025 | Al-Ali et al. |
| 2025/0319257 A1 | 10/2025 | Mazlish et al. |
| 2025/0322950 A1 | 10/2025 | Al-Ali et al. |
| 2025/0323417 A1 | 10/2025 | Rey |
| 2025/0329240 A1 | 10/2025 | Kiani |
| 2025/0344010 A1 | 11/2025 | Al-Ali et al. |
| 2026/0014333 A1 | 1/2026 | Fernkvist et al. |
| 2026/0014334 A1 | 1/2026 | Danwihl |
| 2026/0048198 A1 | 2/2026 | Vo et al. |

OTHER PUBLICATIONS

US 2024/0016391 A1, 01/2024, Lapotko et al. (withdrawn)

Ellingsen et al., "Safety Constraints in an Artificial Pancreatic β Cell: An Implementation of Model Predictive Control with Insulin on Board", Journal of Diabetes Science and Technology, vol. 3, No. 3, May 2009, pp. 536-544.

* cited by examiner

APPLICATOR FOR DISEASE MANAGEMENT SYSTEM

FIELD OF THE DISCLOSURE

The general field of this disclosure is glucose sensing and Disease Management Systems.

BACKGROUND

Diabetes is a chronic disease that impacts many individuals, both adults and children. The management of diabetes may include the measurement of glucose within the interstitial space including blood and/or interstitial fluid of a patient and administration of insulin to the patient. A closed loop insulin administration system includes both a sensor to take glucose measurements from the interstitial space including blood and/or interstitial fluid of the patient and an insulin administration device which administers insulin to the patient based on the glucose measurements. Closed loop insulin administration systems allow individuals impacted by diabetes to go about daily life with much less worry about their insulin or glucose levels which can vastly improve a diabetic's quality of life.

SUMMARY

Various aspects of systems, methods and devices within the scope of the appended claims each have several aspects, no single one of which is solely responsible for the desirable attributes described herein. Without limiting the scope of the appended claims, some prominent features are described herein.

In some aspects, a method of applying a disease management system to a patient using an insertion mechanism, the method comprising: placing a disease management system over an insertion site of a patient; applying pressure to a top surface of the disease management system; removing pressure from the top surface of the disease management system; and using the disease management system and the insertion mechanism.

In some aspects, the disease management system includes an adhesive layer configured to couple the disease management system to the patient upon application of pressure to the top surface of the disease management system.

In some aspects, applying pressure to the top surface of the disease management system activates the insertion mechanism.

In some aspects, activation of the insertion mechanism comprises inserting a needle and an implantable component into the patient.

In some aspects, activation of the insertion mechanism further comprises exerting a spring force to retract the needle from the patient.

In some aspects, the disease management system is applied to the patient for a semi-extended period of time.

In some aspects, the disease management system is applied to the patient for a useful lifespan of the disease management system.

In some aspects, the disease management system is applied to the patient for approximately 1 day to about 8 days.

In some aspects, pressure is applied in a direction of the insertion site.

In some aspects, a method of inserting an implantable component that is part of a disease management system into an insertion site of a patient, the method comprising: receiving a force in a direction of the insertion site applied to a top portion of a disease management system; unlocking an insertion spring lock with the force applied in the direction of the insertion site to cause an insertion spring to expand from a compressed state of the insertion spring; inserting a needle and implantable component coupled to the insertion spring into the insertion site from expansion of the insertion spring; unlocking a retraction spring lock with the force generated from expansion of the insertion spring to cause a retraction spring to expand from a compressed state of the retraction spring; and retracting the needle with force generated from expansion of the retraction spring while leaving the implantable component in the insertion site.

In some aspects, the needle and implantable component are in a retracted position when the disease management system is in an unloaded state.

In some aspects, the needle and implantable component are inserted into the insertion site when the disease management system is in a loaded state.

In some aspects, the needle and implantable component are inserted into the insertion site at a depth of approximately 2.5 mm to about 6 mm.

In some aspects, the force applied to the disease management system in the direction of the insertion site is between approximately 0.020 kgf to about 0.560 kgf.

In some aspects, a system of inserting an implantable component into an insertion site of a patient, the system comprising: an insertion spring; an insertion spring lock configured to hold the insertion spring in a compressed state when in a locked state; a retraction spring configured to fit inside the insertion spring and coupled to a portion of the insertion spring; a needle coupled to the retraction spring; and an implantable component coupled to the needle, wherein the insertion spring lock is configured to release in order to decompress the insertion spring and insert the needle and implantable component when a force is applied to the system towards the insertion site of the patient, and wherein the retraction spring is configured to release in order to decompress the retraction spring and retract the needle without the implantable component when the insertion spring is decompressed.

In some aspects, the system further comprises an adhesive layer configured to adhere the system to a patient's skin.

In some aspects, the needle and implantable component are in a retracted position when the system is in an unloaded state.

In some aspects, the needle and implantable component are inserted into the insertion site when the system is in a loaded state.

In some aspects, the needle and implantable component are inserted into the insertion site at a depth of approximately 2.5 mm to about 6 mm.

In some aspects, the force applied to the system is between approximately 0.020 kgf to about 0.560 kgf.

In some aspects, a system configured to insert an implantable component of a disease management system into an insertion site of a patient, the system comprising: a pressure source configured to apply pressure to a top surface of the disease management system to activate an insertion mechanism of the disease management system.

BRIEF DESCRIPTION OF THE DRAWINGS

To easily identify the discussion of any particular element or act, the most significant digit or digits in a reference number refer to the figure number in which that element is first introduced.

DETAILED DESCRIPTION

Figure 1:
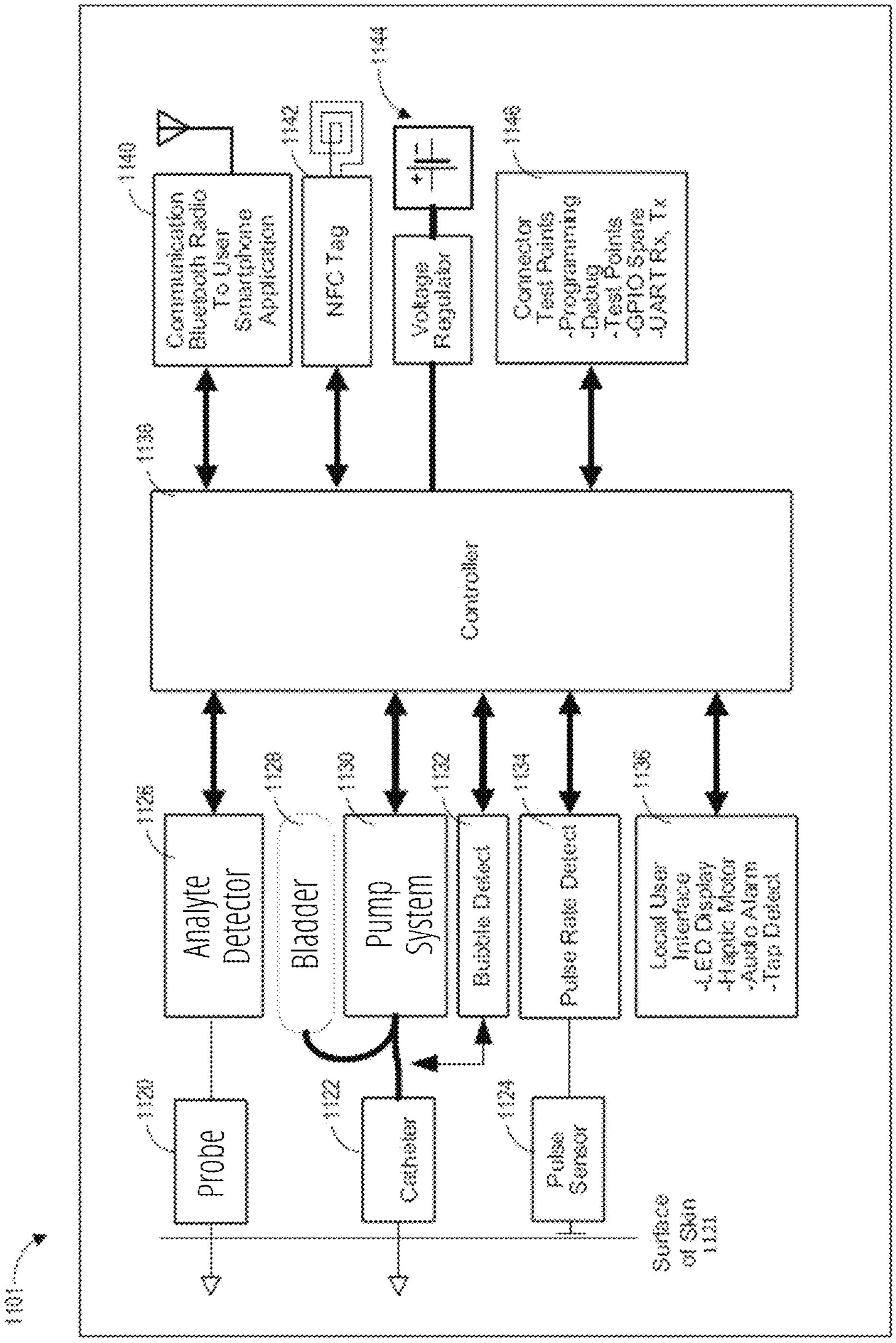
FIG. 1 illustrates an example disease management system that may be included in a disease management environment or used as an interleaved device.

FIG. 1 shows a block diagram of an example Disease Management System 1101. In some examples, the disease management system 1101 may be part of a disease management environment, such as described above. A disease management system 1101 may be configured to measure one or more physiological parameters of a patient (such as pulse, skin temperature, or other values), measure one or more analytes present in the blood of a patient (such as glucose, lipids, or other analyte) and administer medication (such as insulin, glucagon, or other medication). In some examples, a disease management system 1101 may be configured to communicate with one or more hardware processors that may be external to the disease management system 1101, such as a cloud based processor or user device. A disease management system 1101 may include an NFC tag to support authentication and pairing with a user device (for example, smart phone or smart watch), Bluetooth communication with additional disease management systems or devices, and Bluetooth communication with a paired user device running an associated control application. To support ease of use and safe interaction with the patient, the system may incorporate user input through a tap-detecting accelerometer and provide feedback via an audio speaker, haptic vibration, and/or optical indicators. The system may operate on battery power and support both shelf-life and reliable operation once applied to the patient. Battery life may be managed through control of several planned levels of sleep and power consumption. To support this reliability, a controller can monitor several system-health parameters, and monitor temperatures of the included medication, and ambient temperature for the life of the device.

As illustrated in FIG. 1, a controller 1138 of the disease management system 1101 may be configured to communicate and control one or more components of the disease management system 1101. The controller 1138 may include one or more hardware processors, such as a printed circuit board (PCB) or the like. The controller 1138 may be configured to communicate with peripheral devices or components to support the accurate measurement of physiological parameters and blood analytes, such as patient pulse, temperature, and blood glucose, using detector electronics. The controller 1138 may subsequently calculate dose or receive a calculated dose value and administer medication, such as insulin, by actuation of an actuated pump. The controller 1139 may record device activity and transfer the recorded data to non-volatile secure memory space. At the end of the life of a device or system, the controller can be configured to lock operation, and create a data recovery module to permit authenticated access to the recorded data if needed.

A disease management system 1101 may include an analyte sensor 1120. The analyte sensor 1120 may be configured to detect analytes in the patient's blood. For example, an analyte sensor 1120 can include a glucose sensing probe configured to pierce the surface of the skin 1121. In some examples, a disease management system 1101 may include a plurality of analyte sensors 1120 to detect one or more analytes. In some examples, an analyte sensor 1120 may be configured to detect a plurality of analytes. Sensed analytes may include, but are not limited to, glucose, insulin, and other analytes. An analyte sensor 1120 may be configured to communicate with an analyte detector 1126. The analyte detector 1126 may be configured to receive a signal of one or more analyte sensors 1120 in order to measure one or more analytes in the blood of the patient. The analyte detector 1126 may be configured to communicate with the controller 1138. For example, the analyte detector 1126 may be configured to, for example, send analyte values to the controller 1138 and receive control signals from the controller.

A disease management system 1101 may include a medication catheter 1122. The medication catheter 1122 may be configured to administer medication, including, but not limited to insulin, to the patient. The medication catheter 1122 may receive medication from a medication bladder 1128 configured to contain medication to be administered. The medication bladder 1128 may be configured to contain medication for a prolonged period, such as 1 day, 3 days, 6 days, or more. The medication bladder 1128 may be configured to contain certain medication types, such as insulin. In some examples, a disease management system 1101 may include a plurality of medication bladders 1128 for one or more reservoirs of the same or different medications. In some examples, a disease management system 1101 may be configured to mix medications from medication bladders 1128 prior to administration to the patient. A pump system 1130 may be configured to cause medication to be administered from the bladder 1128 to the patient through the insulin catheter 1122. A pump system 1130 may include, but is not limited to, a pump, such as a nitinol wire pump or other pump configured to deliver medication to the patient from the bladder 1128 through the catheter 1122 (also sometimes referred to as a cannula).

A disease management system 1101 may optionally include a physiological sensor. A physiological sensor may include a pulse rate sensor, such as a pulse rate sensor 1124, temperature sensor, pulse oximeter, the like or a combination thereof. In some examples, a disease management system 1101 may be configured to include a plurality of physiological sensors. The pulse rate sensor 1124 may be configured to communicate with a pulse rate detector 1134. The pulse rate detector 1134 may be configured to receive a signals of the pulse rate sensor 1124. The pulse rate detector 1134 may be configured to measure or determine and communicate a physiological value from the signal. The pulse rate detector 1134 may be configured to communicate with the controller 1138. For example, the pulse rate detector 1138 may be configured to, for example, send measured physiological values to the controller 1138 and receive control signals from the controller.

disease management system 1101 may include one or more local user interfacing components 1136. For example, a local user interfacing component 1136 may include, but is not limited to one or more optical displays, haptic motors, audio speakers, and user input detectors. In some examples, an optical display may include an LED light configured to display a plurality of colors. In some examples, an optical display may include a digital display of information associated with the Disease Management System 1101, including, but not limited to, device status, medication status, patient status, measured analyte or physiological values, the like or a combination thereof. In some examples, a user input detector may include an inertial measurement unit, tap detector, touch display, or other component configured to accept and receive user input. In some examples, audio speakers may be configured to communicate audible alarms related to device status, medication status user status, the like or a combination thereof. A controller 1138 may be configured to communicate with the one or more local interfacing components 1136 by, for example, receiving user input from the one or more user input components or sending control signals to, for example, activate a haptic motor, generate an output to the optical display, generate an audible output, or otherwise control one or more of the local user interfacing components 1136.

A disease management system 1101 may include one or more communication components 1140. A communication component 1140 can include, but is not limited to one or more radios configured to emit bluetooth, cellular, wi-fi, or other wireless signals. In some examples, a communication component 1140 can include a port for a wired connection. Additionally, a disease management system 1101 may include an near field communication ("NFC") tag 1142 to facilitate in communicating with one or more hardware processors. The one or more communication components 1140 and NFC tag 1142 may be configured to communicate with the controller 1138 in order to send and/or receive information associated with the disease management system 1101. For example, a controller 1138 may communicate medication information and measured values through the one or more communication components 1140 to an external device. Additionally, the controller 1138 may receive instructions associated with measurement sampling rates, medication delivery, or other information associated with operation of the management system 1101 through the one or more communication components 1140 from one or more external devices.

A disease management system 1101 may include one or more power components 1144. The power components may include, but are not limited to one or more batteries and power management components, such as a voltage regulator. Power from the one or more power components 1144 may be accessed by the controller and/or other components of the Disease Management System 1101 to operate the disease management system 1101.

A disease management system 1101 may have one or more power and sleep modes to help regulate power usage. For example, a disease management system 1101 may have a sleep mode. The sleep mode may be a very low power mode with minimal functions, such as the RTC (or real time clock) and alarms to wake the system and take a temperature measurement of the system, or the like. In another example, a disease management system 1101 may include a measure temperature mode which may correspond to a low power mode with reduced functions. The measure temperature mode may be triggered by the RTC where the system is configured to take a temperature measurement, save the value, and return the system to a sleep mode. In another example, a disease management system 1101 may include a wake up mode. The wake up mode may be triggered by an NFC device and allow the system to pair with an external device with, for example, bluetooth. If a pairing event does not occur, the system may return to sleep mode. In another example, a disease management system 1101 may include a pairing mode. The pairing mode may be triggered by an NFC device. When a controlling application is recognized, the system may proceed to pair with the application and set the system to an on condition and communicate to the cloud or other external device to establish initial data movement. In another example, a disease management system 1101 may include a rest mode where the system is configured to enter a lower power mode between measurements. In another example, a disease management system 1101 may include a data acquisition mode where the system is configured to enter a medium power mode where data acquisition takes place. In another example, a disease management system 1101 may include a parameter calculation mode where the system is configured to enter a medium power mode where parameter calculations, such as a blood glucose calculations, are performed and data is communicated to an external device and/or the cloud. In another example, a disease management system 1101 may include a pump mode where the system is configured to enter a higher power mode where the pump draws power to deliver medication to the patient.

A disease management system 1101 may include one or more connector test points 1146. The connecter test points may be configured to aid in programming, debugging, testing or other accessing of the disease management system 1101. In some examples, connector test points 1146 may include, for example, a GPIO spare, UART receiver or transmitter, the like or a combination thereof.

Figure 2:
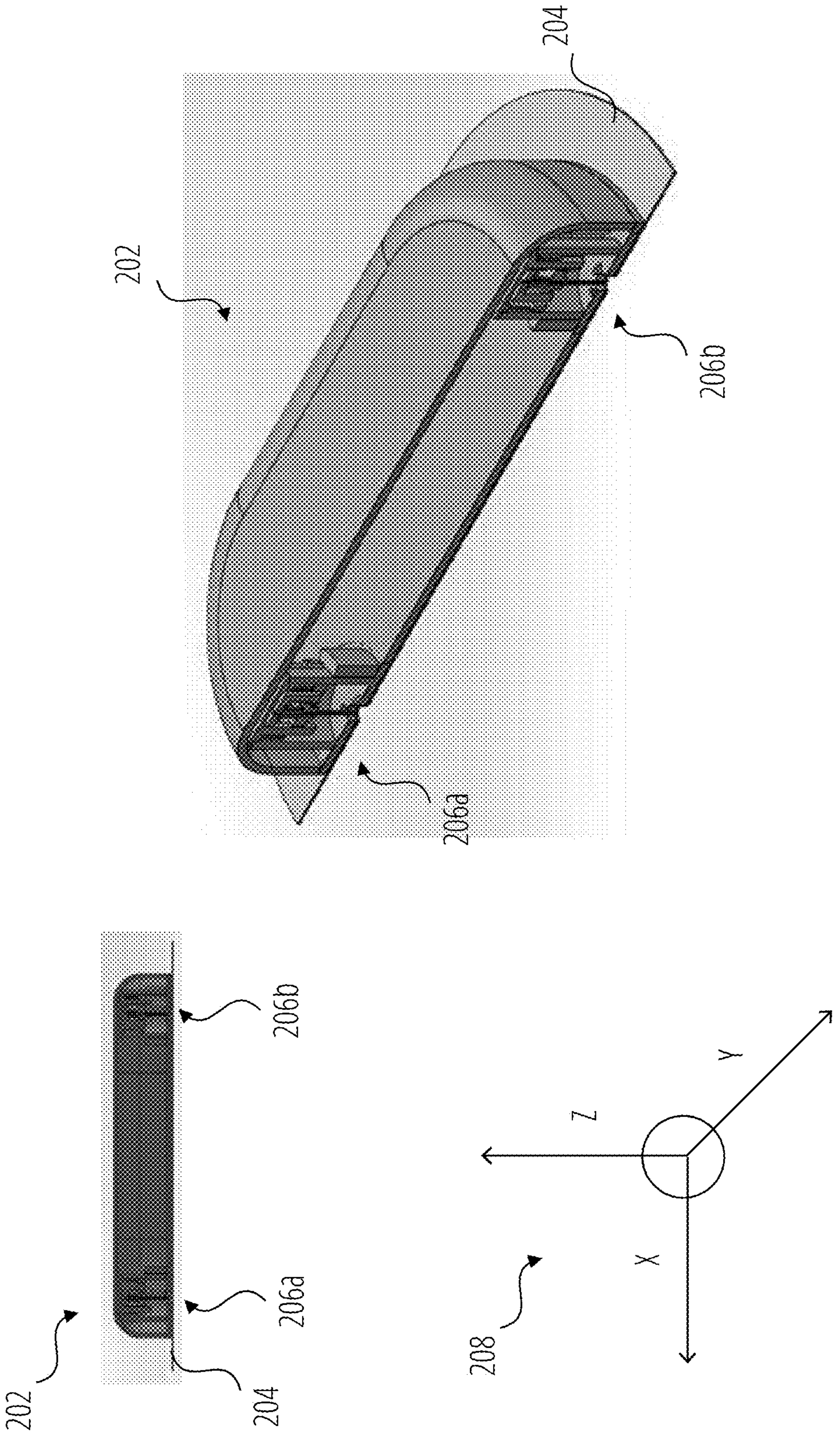
FIG. 2 illustrates perspective vies of an example applicator system.

FIG. 2 illustrates a example of an applicator 202. An applicator 202 may be part of a disease management system. As illustrated in FIG. 2, an applicator 202 can include a combination of an adhesive 204, and one or more insertion mechanisms 206*a*, 206*b*. In some aspects, the adhesive 204 may be located on a bottom side of the applicator 202. This can secure or temporarily secure the applicator 202 to a patient.

The adhesive 204 may be configured to provide adhesion for a prolonged period. For example, the adhesive may be configured to adhere the applicator 202 to the skin of a patient for a period of 1 day, 3 days, 6 days, or more or fewer days or hours. In some examples, the adhesive layer may be configured to have an adhesive force sufficient to prevent accidental removal or movement of the applicator or disease management system during the intended period of use of the disease management system. In some examples, the adhesive 204 may be a single layer of adhesive across at least a portion of a surface the applicator 202 that is configured to interface with the patient. In some examples, the adhesive 204 may include a plurality of adhesive areas on a surface of the applicator 202 that is configured to interface with the patient. In some examples, the adhesive 204 may be configured to be breathable, even when applied to the patient's skin. The applicator 202 can adhere to the patient's skin after wetting the adhesive 204. For example, the adhesive 204 may become wet by humidity or adding liquids such as tap water, saltwater, and chlorinated water to the adhesive 204. A thickness of the adhesive may be, for example, in a range of approximately 0.1 to 0.5 mm or in a range of more or less thickness.

One or more insertion mechanisms 206*a*, 206*b* may be configured to insert and retract one or more needles associated with a component configured to implant the component into the tissue of a patient. For example, a component or implantable component may include a cannula for delivery port of medication to a patient or an analyte sensor. An insertion mechanism may be configured to be part of or enclosed within a structure of the applicator 202. For example, an insertion mechanism may be configured to operate within the structure of the applicator 202. This can minimize the number of individualized or separate components that may be needed to deliver a medication to a patient. Advantageously, this may facilitate an easier application and use of a disease management system for a patient by providing the patient with a minimal number of components to operate. This can result in fewer errors in application or use of the disease management system. Additionally or alternatively, having a single component that includes other components of a disease management system can be easier to manufacture, and can reduce packaging size, reduce manufacturing cost, and improve sterility of the product over a design with a separate applicator or with individualized and separate components. FIGS. 3-6 illustrate further details of the operation and components of an example insertion mechanism.

A coordinate frame 208 is illustrated in FIG. 2 for ease of description. As will be described in further detail below, a user may place an adhesive 204 onto a desired tissue site. The user may then apply a pressure in a direction of the insertion site, or in a Z-direction, to press the applicator 202 to the implantation site of the patient or user. Applying pressure in the Z-direction may ease the insertion of the inserted component by minimizing the pain or lack of comfort the patient may experience during the insertion process, and minimizing the length of the inserted component implanted into the patient. Additionally or alternatively, applying a pressure in the Z-direction allows a component of the applicator to insert into tissue of the patient that is directly underneath the implantation site intended and/or visible to the user. Additionally or alternatively, applying pressure in the Z-direction can minimize the overall surface area of the implantation site. The pressure can serve to activate internal insertion spring(s) and implant one or more needles and implantable components into the patient. Once insertion spring(s) are extended, one or more retraction springs may be activated to remove the one or more needles from the implantation site while leaving the one or more implantable components in place.

Figure 3A:
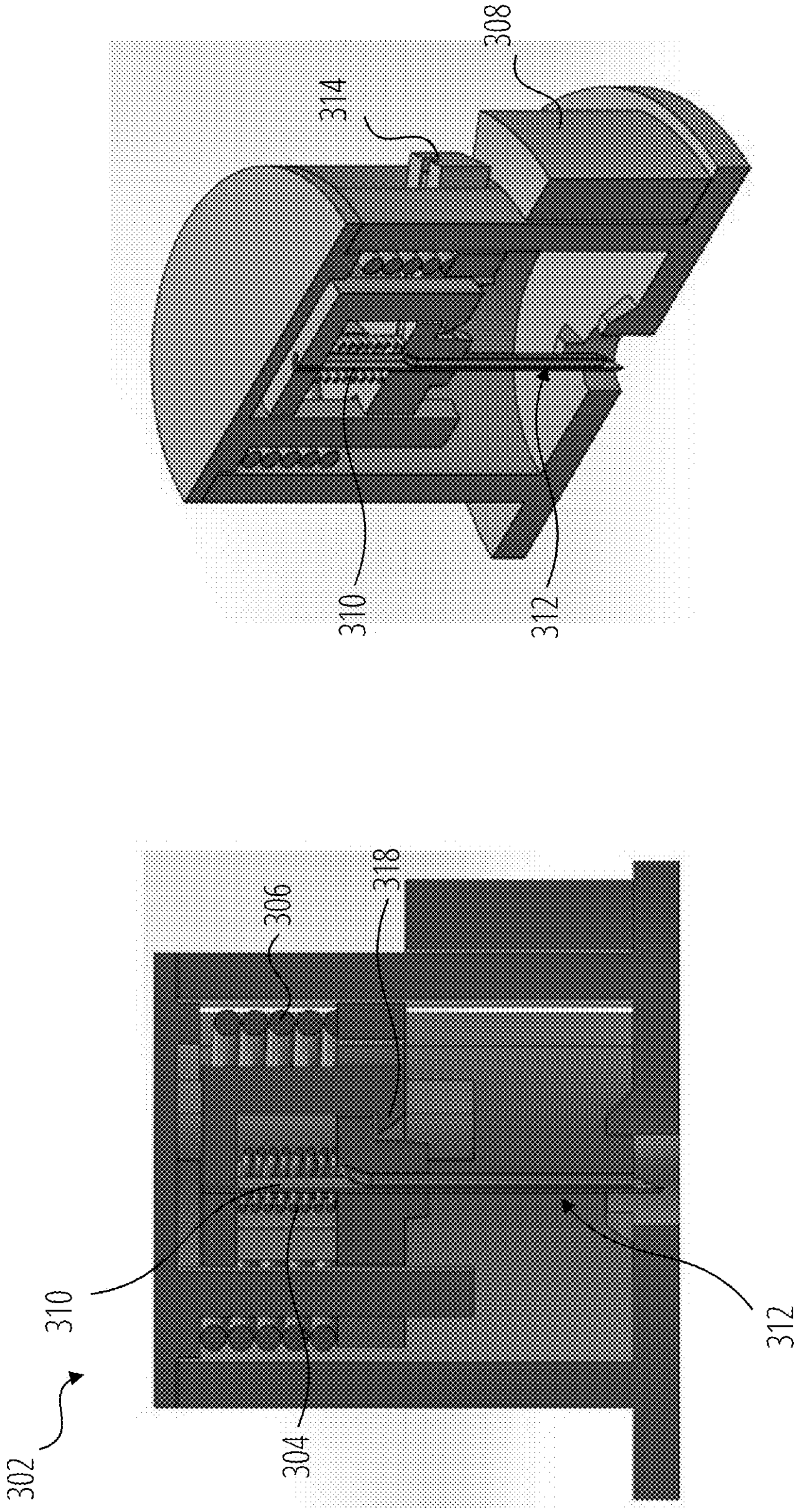
FIG. 3A illustrates an example loaded state of an example applicator system.
Figure 3B:
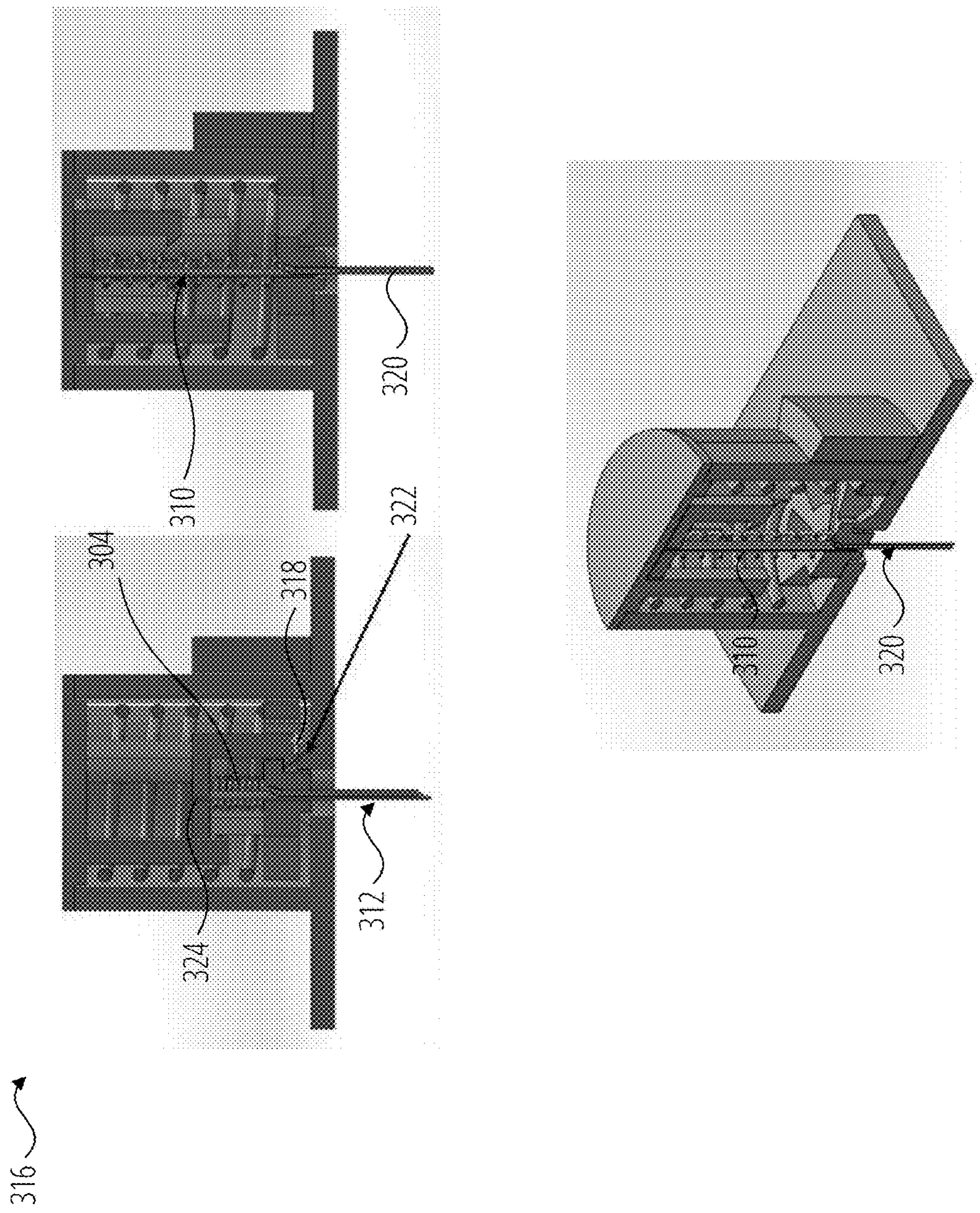
FIG. 3B illustrates an example unloaded state of an example applicator system.

FIG. 3A illustrates an example loaded state 302 of an insertion mechanism and FIG. 3B illustrates an example insertion mechanism 316 in unloaded state. The loaded state 302 may be associated with an unused or unapplied applicator. An applicator may come from manufacture in a loaded state 302. An unloaded state may be associated with an applied or used applicator or disease management system.

With reference to FIG. 3A, in a loaded state 302, a needle and implantable component 312 may be retracted fully or at least with a majority of length of the needle and implantable component 312 within the body of applicator or disease management system. The needle and implantable component 312 may be held in place at least in part by an insertion spring lock 308. The insertion spring lock may assist in controlling when the needle and implantable component 312 is inserted into the patient. Additionally or alternatively, the insertion spring lock can help to ensure the needle and implantable component 312 may not be accidentally unloaded or inserted into the patient. When pressure is applied in a direction of the insertion site, or a Z direction, to a lever 314 connected to the insertion spring lock 308, the compressed or retracted spring lock 318 may be configured to release or extend from its compressed state. For example, the lever 314 may have a first position that corresponds to the spring lock 318 having a retracted position. The lever 314 may have a second position that corresponds to the spring lock 318 having an unretracted position. It is not until pressure is applied to the lever 314 that the lever 314 in the first position moves to the second position. The force resulting from the pressure applied to the lever 314 may drive the needle and implantable component 312 into the tissue of the patient. The needle and implantable component 312 may enter the tissue of the patient as the lever 314 is transitioning from the first position to the second positioned. During the transition, the percentage of the needle and implantable component inserted into the tissue of the patient may be <100%. For example, 0%, 5%, 25%, 80%, etc. The percentage of the needle and implantable component 312 may be inserted into the tissue of the patient may be ≤100% at the second position of the lever 314.

In some examples, a needle 310 may be inserted at different depths based on a patient age, weight, or other parameter. For example, a depth of insertion of a medication cannula may be approximately 3 mm for 7 to 12 year olds. In another example, a depth of insertion of a medication cannula may be approximately 4 mm for 13 year olds and older. In another example, a depth of insertion of a medication needle 310 may be approximately 4 to 4.5 mm for 7 to 12 year olds. In another example, a depth of insertion of a medication needle 310 may be approximately 5 to 5.5 mm for 13 year olds and older. In another example, a depth of insertion of an analyte sensor may be approximately 3 mm for 7 to 12 year olds. In another example, a depth of insertion of an analyte sensor may be approximately 4 mm for 13 year olds and older. In another example, a depth of insertion for a needle associated with an analyte sensor may be approximately 4 to 4.5 mm for 7 to 12 year olds. In another example, a depth of insertion for a needle associated with an analyte sensor may be approximately 5 to 5.5 mm for 13 year olds and older. However, other values or ranges for any of the inserted components are also possible.

With reference to FIG. 3B, once the needle and implantable component 312 is inserted into the patient, a retraction spring lock 318 may disengage. The retraction spring lock 318 may be configured to disengage when expansion force from the insertion springs 306 presses the retraction spring lock 318 against an engagement mechanism 322. For example, the insertion springs 306 may include a plurality of coils. The distance between each coil may increase allowing the needle and implantable component 312 to insert into the patient and the retraction spring lock 318 to contact the engagement mechanism 322 located near a bottom of an insertion mechanism 316. The engagement mechanism 322 may move the retraction spring lock 318 in a direction parallel to the bottom of the insertion mechanism 316, for example, in an X-direction. The engagement mechanism 322 may move the retraction spring lock 318 from a center of the insertion mechanism 316 and allow a retraction spring 304, connected to the retraction spring lock 318, to expand or decompress. The needle 310 may be coupled to an end portion 324 of the retraction spring 304 such that as the retraction spring lock 318 expands, the needle 310 is retracted or lifted out of the patient and into the body of the insertion mechanism or disease management system while leaving the implantable component 320 in the patient. This can minimize the amount of time the needle 310 is inside the tissue of the patient. This can also help to ensure the surface area of the implantation site is minimized because the needle 310 can exit the tissue of the patient in the same or similar path at which it entered the tissue of the patient. This can help to minimize error that may arise from use of the applicator or disease management system.

Figure 4:
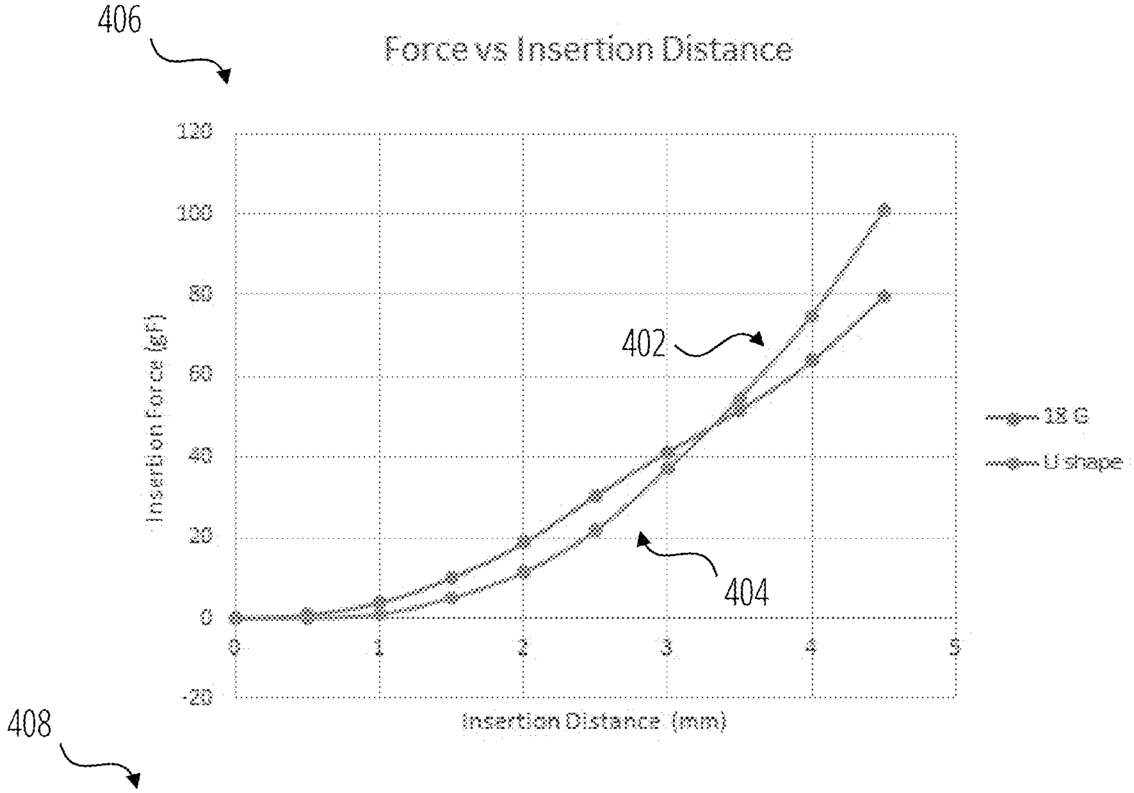
FIG. 4 illustrates an example insertion force for an example applicator system.

FIG. 4 illustrates an example Graph 406 of an example insertion force with respect to insertion distance for different needle types. For example, a line 402 shows an insertion force with respect to insertion distance for an 18 gauge needle and a line 404 shows an insertion force with respect to insertion distance for a U shape needle.

A choice of insertion spring may be based on a measured or determined insertion force and/or how far the needle and/or implantable component should be inserted into the patient.

For example, an insertion force may be associated with a spring constant of a spring.

A minimum force of a spring can be determined as:

$$F_{min}=\text{Rate}_{Spring}\times(\text{Free\_length}-\text{loaded\_length}-\text{needle\_moving\_distance})$$

A maximum force of a spring can be determined as:

$$F_{max}=\text{Rate}_{Spring}\times(\text{Free\_length}-\text{loaded\_length})$$

Where a free length is 7.95 mm, a spring rate is 0.025 kgf/mm, a solid length of the needle is 2.06 mm, a spring displacement is function of design force and spring rate and is 2.8 mm, a loaded length is 2.1 mm, and a needle moving distance is 5 mm, a minimum force is 0.021 kgf and a maximum force is 0.146 kgf. A spring could then be selected based on these parameters. Similarly, where a free length is 12.5 mm, a spring rate is 0.058 kgf/mm, a solid length of the needle is 2.54 mm, a spring displacement is function of design force and spring rate and is 3.448 mm, a loaded length is 3 mm, and a needle moving distance is 5 mm, a minimum force is 0.0261 kgf and a maximum force is 0.551 kgf. A spring could then be selected based on these parameters.

Figure 5:
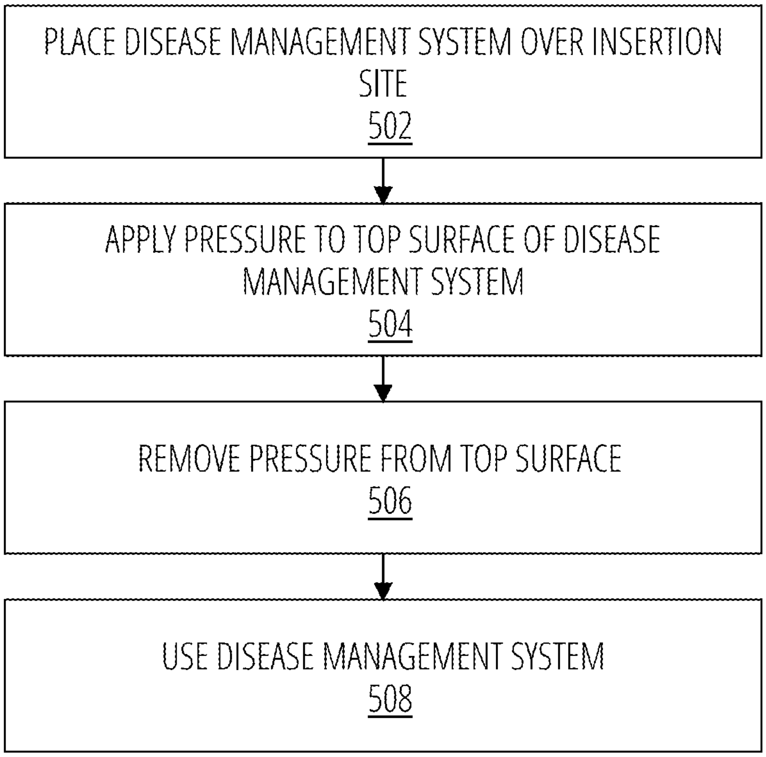
FIG. 5 is a block diagram illustrating an example aspect of applying a disease management system using an example applicator system.

FIG. 5 illustrates a block diagram of an example application of a disease management system to a user using an insertion mechanism such as described herein. At a block 502, a user may place a disease management system over a desired insertion site. The disease management system may be in a loaded state such that the needles and implantable components are not yet deployed. The user may place the disease management system such that an adhesive component of the disease management system may couple the disease management system to the tissue of the patient. At a block 504, a user may apply pressure in a direction of the insertion site to a top surface of disease management system. The pressure may activate the insertion mechanism and insert the needle and implantable component into the patient and retract the needle such as described above. The retraction of the needle may be instantaneous. At block 506, a user may remove pressure from the top surface of the disease management system. At block 508, the user may proceed with using the disease management system, which may be applied to the user for a semi-extended period or the useful life of the disease management system. This time frame can include a plurality of days, such as 3 days, 6 days, or more or fewer days.

Figure 6:
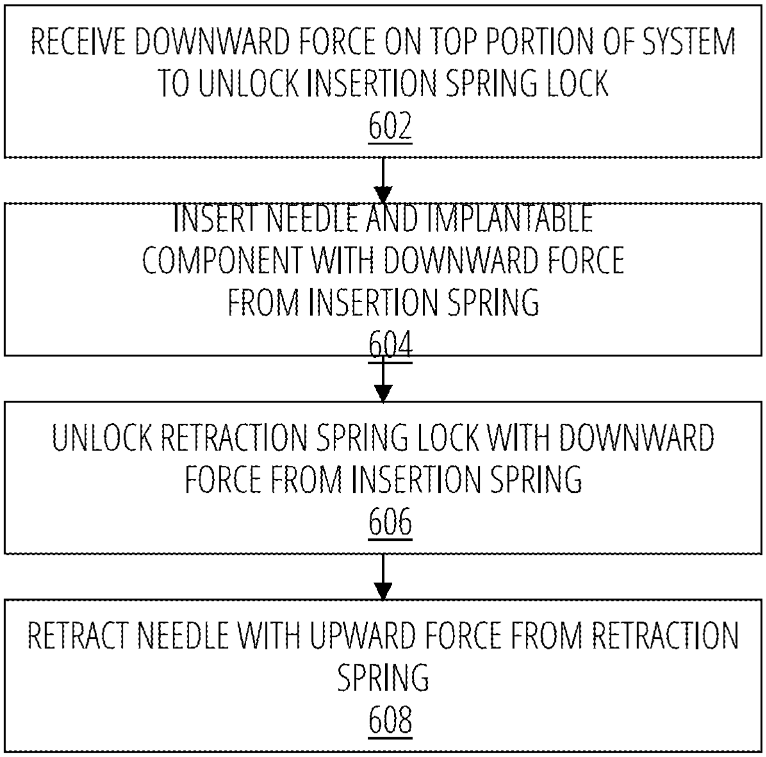
FIG. 6 is a block diagram illustrating an example method of operation of an example applicator system.

FIG. 6, illustrates a block diagram of an example insertion process of an implantable component using an insertion mechanism. At a block 602, a top portion of a disease management system may receive a force applied in the direction of an implantation site. This force may unlock an insertion spring lock configured to hold an insertion spring in a compressed state. A needle and implantable component may additionally be held in a retracted state while the insertion spring lock is locked. At block 604, the insertion spring may decompress, inserting the needle and implantable component into the tissue of the patient with force exerted from the decompressing insertion spring in the direction of the implantation site. In a block 606, the downward force of the decompressing insertion spring may unlock a retraction spring lock. The retraction spring lock may be configured to hold the retraction spring in a compressed state when locked. In a block 608, a force of the retraction spring decompressing may retract a needle into the body of the disease management system, while the implantable component remains in the tissue of the patient.

Terminology

While the above description has pointed out novel features of the invention as applied to various embodiments, the skilled person will understand that various omissions, substitutions, and changes in the form and details of the device or process illustrated may be made without departing from the scope of the invention. Therefore, the scope of the invention is defined by the appended claims rather than by the foregoing description. All variations coming within the meaning and range of equivalency of the claims are embraced within their scope.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Embodiments of the disclosed systems and methods can be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. A method of applying a disease management system to a patient using an insertion mechanism, the method comprising:

placing a disease management system over an insertion site of a patient;

applying pressure to a top surface of the disease management system in a direction substantially perpendicular to the top surface, thereby unlocking an insertion spring lock by transmitting the applied pressure to a lever actionably connected to the insertion spring lock, thereby causing an insertion spring to expand from a compressed state to deploy a needle;

removing pressure from the top surface of the disease management system; and using the disease management system.

2. The method of claim 1, wherein the disease management system includes an adhesive layer configured to couple the disease management system to the patient upon application of pressure to the top surface of the disease management system.

3. The method of claim 1, wherein applying pressure to the top surface of the disease management system activates the insertion mechanism.

4. The method of claim 3, wherein activation of the insertion mechanism comprises inserting a needle and an implantable component into the patient.

5. The method of claim 4, wherein activation of the insertion mechanism further comprises exerting a spring force to retract the needle from the patient.

6. The method of claim 1, wherein the disease management system is applied to the patient for a semi-extended period of time.

7. The method of claim 1, wherein the disease management system is applied to the patient for a useful lifespan of the disease management system.

8. The method of claim 1, wherein the disease management system is applied to the patient for approximately 1 day to about 8 days.

9. The method of claim 1, wherein pressure is applied in a direction of the insertion site.

10. A method of inserting an implantable component that is part of a disease management system into an insertion site of a patient, the method comprising:

receiving a force applied in a direction substantially perpendicular to a top surface of a top portion of a disease management system;

unlocking an insertion spring lock by transmitting the received force to a lever actionably connected to the insertion spring lock, thereby causing an insertion spring to expand from a compressed state;

inserting, caused by expansion of the insertion spring, a needle and an implantable component coupled to the insertion spring into the insertion site;

unlocking, caused by force generated by the expansion of the insertion spring, a retraction spring lock, thereby causing a retraction spring to expand from a compressed state; and retracting, caused by force generated by the retraction spring, the needle, wherein the implantable component remains within the insertion site after retraction of the needle.

11. The method of claim 10, wherein the needle and the implantable component are in a retracted position when the disease management system is in an unloaded state.

12. The method of claim 10, wherein the needle and the implantable component are inserted into the insertion site when the disease management system is in a loaded state.

13. The method of claim 10, wherein the needle and the implantable component are inserted into the insertion site at a depth of approximately 2.5 mm to about 6 mm.

14. The method of claim 10, wherein the force applied to the disease management system in the direction of the insertion site is between approximately 0.020 kgf to about 0.560 kgf.

15. A system of inserting an implantable component into an insertion site of a patient, the system comprising:

an insertion spring;

an insertion spring lock configured to hold the insertion spring in a compressed state when in a locked state;

a lever configured to transmit force received in a direction substantially perpendicular to a top surface of the system to the insertion spring lock so as to unlock the insertion spring lock;

a retraction spring configured to fit inside the insertion spring and coupled to a portion of the insertion spring;

a needle coupled to the retraction spring; and an implantable component coupled to the needle, wherein the insertion spring lock is configured, when unlocked, to release and allow decompression of the insertion spring and insert the needle and implantable component into the insertion site, and wherein the retraction spring is configured to decompress in response to force generated by the decompression of the insertion spring, the retraction spring configured to retract the needle without the implantable component when the insertion spring is decompressed.

16. The system of claim 15, further comprising an adhesive layer configured to adhere the system to a patient's skin.

17. The system of claim 15, wherein the needle and the implantable component are in a retracted position when the system is in an unloaded state.

18. The system of claim 15, wherein the needle and the implantable component are inserted into the insertion site when the system is in a loaded state.

19. The system of claim 15, wherein the needle and the implantable component are inserted into the insertion site at a depth of approximately 2.5 mm to about 6 mm.

20. The system of claim 15, wherein the force applied to the system is between approximately 0.020 kgf to about 0.560 kgf.

21. The system of claim 15, wherein the needle and implantable component are configured to enter the insertion site when the lever is transitioning from a first position to a second position.

* * * * *